United States Patent
Wang et al.

(10) Patent No.: US 11,866,759 B1
(45) Date of Patent: Jan. 9, 2024

(54) **METHOD OF PRODUCING CALCIUM PROPIONATE BY USING *LACTOBACILLUS REUTERI***

(71) Applicant: SHENZHEN AGRECOE BIOTECHNOLOGY CO., LTD., Guangdong (CN)

(72) Inventors: Jianying Wang, Guangdong (CN); Zongyao Kong, Guangdong (CN)

(73) Assignee: SHENZHEN AGRECOE BIOTECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 18/302,911

(22) Filed: Apr. 19, 2023

(30) Foreign Application Priority Data

Jun. 24, 2022 (CN) .......................... 202210725513.3

(51) Int. Cl.
*C12P 7/52* (2006.01)
*C12N 9/04* (2006.01)
*C12N 1/20* (2006.01)
*C12N 15/01* (2006.01)

(52) U.S. Cl.
CPC .............. *C12P 7/52* (2013.01); *C12N 1/205* (2021.05); *C12N 9/0006* (2013.01); *C12N 15/01* (2013.01); *C12Y 101/01001* (2013.01)

(58) Field of Classification Search
None
See application file for complete search history.

(56) References Cited

U.S. PATENT DOCUMENTS

2018/0073044 A1* 3/2018 Visser ....................... C12P 7/52

FOREIGN PATENT DOCUMENTS

| CN | 112176005 A | * | 1/2021 | ............... C12N 1/20 |
| CN | 114591994 A | * | 6/2022 | |
| WO | WO-2014102180 A1 | * | 7/2014 | ........... C12N 9/1029 |

OTHER PUBLICATIONS

Zielinska et al., Evaluation of the ability to metabolize 1,2-propanediol by heterofermentative bacteria of the genus *Lactobacillus*, Electronic J. Biotechnol. 26, 2017, 60-63. (Year: 2017).*
Sriramulu et al., Lactobacillus reuteri DSM 20016 Produces Cobalamin-Dependent Diol Dehydratase in Metabolosomes and Metabolizes 1,2-Propanediol by Disproportionation, J. Bacteriol. 190, 2008. 4559-67. (Year: 2008).*
Ju et al., Effective bioconversion of 1,3-propanediol from biodiesel-derived crude glycerol using organic acid resistance-enhanced Lactobacillus reuteri JH83, Biores. Technol. 337, 2021, 125361. (Year: 2021).*
Ottenheim et al., Microbial mutagenesis by atmospheric and room-temperature plasma (ARTP), Bioresour. Bioprocess. 5, 2018, 12. (Year: 2018).*

* cited by examiner

*Primary Examiner* — Todd M Epstein
(74) *Attorney, Agent, or Firm* — COOPER LEGAL GROUP, LLC

(57) ABSTRACT

The present application relates to a technical field of *Lactobacillus* strains, specifically, to a method of producing calcium propionate by using *Lactobacillus reuteri*. The method is that: the *Lactobacillus reuteri* with inactivated alcohol dehydrogenase and 1,2-propanediol are mixed, then grown and reproduced, and then an enrichment culture is conducted; and, after enrichment culture, a strain is placed into a culture medium containing calcium ion for a fermentation culture, then calcium propionate is obtained.

5 Claims, 1 Drawing Sheet

Specification includes a Sequence Listing.

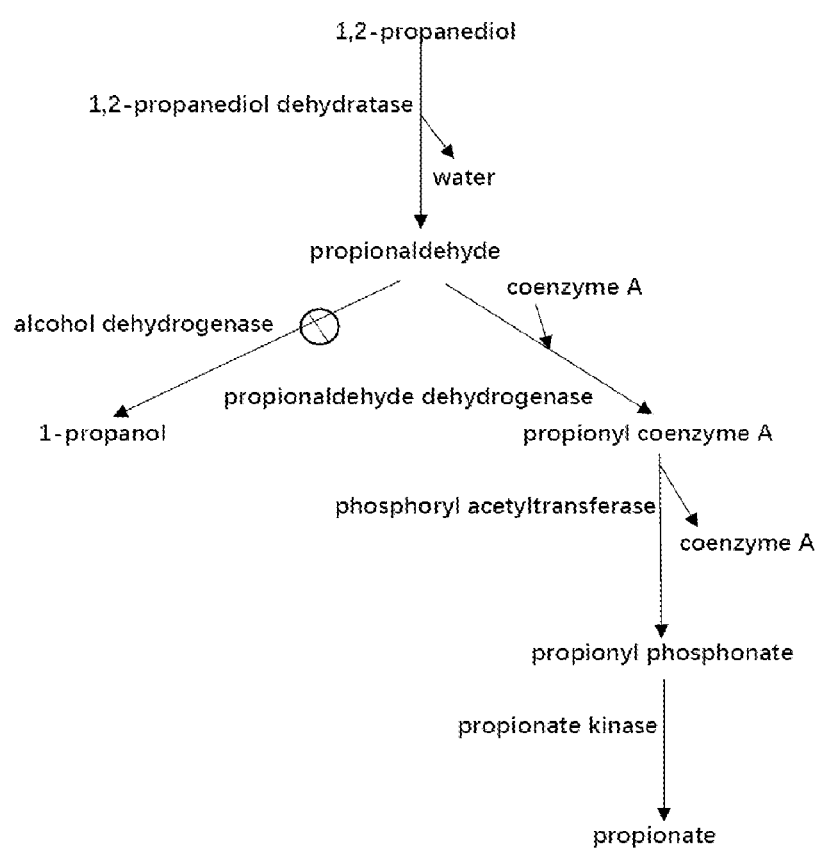

SEQUENCE LISTING

```
Sequence total quantity: 1
SEQ ID NO: 1            moltype = DNA   length = 1122
FEATURE                 Location/Qualifiers
source                  1..1122
                        mol_type = genomic DNA
                        organism = Lactobacillus reuteri
SEQUENCE: 1
ttggaaaaat ttagtatgcc aacccgaatt tattcgggaa cagatagttt gaaggaatta   60
gaaacccttc ataatgaacg aattttgtta gtttgtgact cattcttacc tggtagtgac  120
acattaaagg aaattgagag tcatattaac gacagtaata aatgtgaaat tttctctgat  180
gttgtccctg atccaccact agataaaatt atggaagggg ttcaacagtt cttaaagctg  240
aaaccaacaa ttgtaattgg tatcggtggt ggttctgcaa tggacaccgg taagggaatt  300
cgtttcttcg gtgaaaagct tggcaagtgc aaaattaatg aatatattgc aattccaaca  360
accagcggaa ccggttcaga agttactaat actgcggtta tttctgatac taaggaacac  420
cggaagattc cgattcttga agattactta acaccagatt gtgcattgct tgatcctaag  480
ttagtaatga cagcaccaaa gagtgttact gcctactcag gaatggatgt attaactcat  540
gctcttgaat cattggttgc taaggacgct aatttgttta ccgttgcatt atcagaagaa  600
gccattgatg cggtaactaa gtatcttgtt gaatgttatc gtcatggcga taatgtcgat  660
gcacgaaaga tcgttcacga agcatcaaat attgccggaa cagcctttaa cattgctgga  720
ctaggtatt gccactcaat tgcccaccaa ttaggtgcta acttccatgt tcctcatggt  780
ttagcaaaca caatgttatt gccatatgtt gttgcataca atgctgaaca ctgtgaagaa  840
gccttacaca agtttgcaat tgccgctaag aaagccggaa ttgctgcacc tggcgttggt  900
gaccgtttgg ctgttaagcg gctgattgca aagattcgtg aaatggcacg gcaaatgaat  960
tgtccaatga ctctccaagc atttggagtt gaccacgcaa aagcagaagc agctgctgat 1020
acggttgttg ctaatgcgaa gaaggatgca acattcccag gcaatccagt tgttccttca 1080
gatgatgatc tgaagatgat ttacgaagca ataattcgtt aa                    1122
```

METHOD OF PRODUCING CALCIUM PROPIONATE BY USING *LACTOBACILLUS REUTERI*

CROSS-REFERENCE TO RELATED APPLICATION

The present application is based on and claims the priority benefits of China application No. 202210725513.3, filed on Jun. 24, 2022. The entirety of China application No. 202210725513.3 is hereby incorporated by reference herein and made a part of this specification.

REFERENCE TO AN ELECTRONIC SEQUENCE LISTING

The contents of the electronic sequence listing (SequenceListing.xml; Size: 2,875 bytes; and Date of Creation: Apr. 18, 2023) is herein incorporated by reference.

TECHNICAL FIELD

The present application relates to a technical field of *Lactobacillus* strains, specifically, to a method of producing calcium propionate by using *Lactobacillus reuteri*.

BACKGROUND ART

As a preservative and a chemical intermediate, propionate acid is widely used in food, agriculture and pharmaceutical industry and other fields. Currently, propionate acid is mainly produced by chemical synthesis method in industry. However, resources consumed by chemical synthesis method are non-renewable resources. Meanwhile, the chemical synthesis method is easy to pollute environment. Therefore, a biological method of producing propionate acid by using renewable resources as raw materials is attracting more attention. In addition, with a development of living standards of people, more and more consumers prefer bio-based food preservative. As the most widely used food preservative, a bio-based propionic acid has a great market capacity.

In related technology, a propionic acid biological fermentation process adopts an anaerobic propionic acid *bacillus* process, which not only needs an anaerobic operation and a good equipment condition, but also has a long fermentation period and a low yield. Therefore, developing a new generation synthetic process of bio-based propionic acid, significantly improving a production efficiency and increasing yield are industrial technology development directions of propionic acid.

*Lactobacillus reuteri* often inhabits in an intestinal system of humans and animals, is harmless to humans and animals, and has a better biocompatibility. US FDA has already has certified that the *Lactobacillus reuteri* is a safe and healthy probiotic that can be used as a food supplement. In 2003, Ministry of Health of China has officially approved that the *Lactobacillus reuteri* is a probiotic strain that can be used for health food, and what is more important, a human intake safety of the strain is already confirmed by plurality of the in vitro and animal clinical researches. In addition, the *Lactobacillus reuteri* itself is a good intestinal probiotic, which can partially replace antibiotics for a feed industry, improve an immunity of farmed animals and decrease a loss from a disease. In recent years, it has been found from experiments that the *Lactobacillus reuteri* can be used to prepare a propionate. However, as so far, there are no any related reports on this research and no propionate product prepared by using *Lactobacillus reuteri* as a substrate.

SUMMARY

In order to develop a new generation synthetic process of bio-based propionic acid and successfully preparing propionate using *Lactobacillus reuteri*, the present application provides a method of producing calcium propionate by using *Lactobacillus reuteri*.

In a first aspect, the present application provides a method of producing calcium propionate by using *Lactobacillus reuteri*, adopting the following technical solutions:

a method of producing calcium propionate by using *Lactobacillus reuteri* includes the following steps:
the *Lactobacillus reuteri* with inactivated alcohol dehydrogenase and 1,2-propanediol are mixed, then grown and reproduced, and then an enrichment culture is conducted; and
after enrichment culture, a strain is placed into a culture medium containing calcium ion for a fermentation culture, then calcium propionate is obtained.

In the above technical solutions, 1,2-propanediol is used as a substrate and the *Lactobacillus reuteri* is used as a catalytic agent in the present application. 1,2-propanediol is dehydrated to produce propionaldehyde under a catalysis of the *Lactobacillus reuteri*. Because the alcohol dehydrogenase of the *Lactobacillus reuteri* is inactivated, a route of propionaldehyde producing 1-alcohol dehydrogenase is inhibited. In addition, a coenzyme A is produced during a fermentation process of the *Lactobacillus reuteri*, and under a catalysis of the coenzyme A, propionaldehyde can only be catalyzed to produce propionyl coenzyme A. Meanwhile, when the strains are placed into the culture medium containing calcium ion for the fermentation culture, the propionyl coenzyme A is promoted to remove coenzyme A under an enzymatic catalysis, and quickly converted into calcium propionylphosphonate under a catalysis of phosphoryl acetyltransferase of the *Lactobacillus reuteri*. The calcium propionyl phosphonate is quickly converted into calcium propionate under an action of propionate kinase of the *Lactobacillus reuteri*. It can be known form tests that a concentration of calcium propionate prepared by inactivating the alcohol dehydrogenase of the *Lactobacillus reuteri* is 9.75±0.15 g/L.

In the present application, if the alcohol dehydrogenase of the *Lactobacillus reuteri* is not inactivated, propionaldehyde is prone to be converted into a large amount of 1-propanol under an action of the alcohol dehydrogenase, and only a small amount thereof is converted into calcium propionate, and the concentration of the finally obtained calcium propionate is only about 6.35 g/L. Therefore, in order to inactivate the alcohol dehydrogenase of the *Lactobacillus reuteri*, the present application constructs a route of preparing calcium propionate by using 1,2-propanediol as the substrate, meanwhile the concentrate of calcium propionate prepared by this route is higher than that of calcium propionate prepared before inactivation Optionally, in the present application, the alcohol dehydrogenase of the *Lactobacillus reuteri* is inactivated by gene editing.

Specifically, using 1,2-propanediol as a substrate, an operation route of inactivating the alcohol dehydrogenase of the *Lactobacillus reuteri* by gene editing is as shown in FIG. 1.

Optionally, 1,2-propanediol and the *Lactobacillus reuteri* with inactivated alcohol dehydrogenase are mixed, then grown and reproduced in a seed culture medium at a reproduction temperature of 37° C. for 24 h. A formulation of the seed culture medium is that: a solvent is water, and solutes and concentrations thereof are as follows: 24 g/L of yeast powder, 24 g/L of glucose, 2.4 g/L of ammonium citrate, 6.2 g/L of sodium acetate, 1.8 g/L of dipotassium hydrogen phosphate, 0.16 g/L of manganese sulfate, 0.21 g/L of magnesium sulfate, and 0.8 g/L of polysorbate 80.

Optionally, after 1,2-propanediol and the *Lactobacillus reuteri* with inactivated alcohol dehydrogenase are mixed and grown and reproduced, a liquid culture medium is adopted for the enrichment culture at an enrichment culture temperature of 37° C. A formulation of the liquid culture medium is that the solvent is water, and the solutes and concentrations thereof are as follows: 24 g/L of yeast powder, 7.6 g/L of 1,2-propanediol, 2.4 g/L of ammonium citrate, 6.2 g/L of sodium acetate, 1.8 g/L of dipotassium hydrogen phosphate, 0.16 g/L of manganese sulfate, 0.21 g/L of magnesium sulfate and 0.8 g/L of polysorbate 80.

Optionally, a culture medium for fermentation culture of the strains is a fermentation culture medium, a culture temperature is 37° C., and a culture time is 24 h. A formulation of the fermentation culture medium is that: the solvent is water, and solutes and concentrations thereof are as follows: 24 g/L of yeast powder, 7.6 g/L of 1,2-propanediol, 2.4 g/L of ammonium citrate, 6.2 g/L of sodium acetate, 1.8 g/L of dipotassium hydrogen phosphate, 0.16 g/L of manganese sulfate, 0.21 g/L of magnesium sulfate and 0.8 g/L of polysorbate 80.

In the above technical solutions, the *Lactobacillus reuteri* with inactivated alcohol dehydrogenase can quickly grow and reproduce to increase a number of the strains under a culturing of the seed culture medium. After a reproduction of the strains is completed within a specified time, reproduced strains are placed into the liquid culture medium for the enrichment culture, so that the strains are concentrated in a certain area for easy selection. Selected strains are placed into the fermentation culture medium for the fermentation culture, then calcium propionate is obtained after the fermentation culture.

In the present application, components and specific dosage thereof in the formulations of the seed culture medium, the liquid culture medium and the fermentation culture medium are provided. It can be seen from experiments that, only when an additional amount of the components and is controlled and the formulations of different culture medium are coordinated with each other, calcium propionate with a high content can be prepared finally.

Optionally, first, the *Lactobacillus reuteri* with inactivated alcohol dehydrogenase is mutated by an atmospheric room temperature plasma mutation technology, then a mutated *Lactobacillus reuteri* with inactivated alcohol dehydrogenase and 1,2-propanediol are mixed.

In the above technical solutions, the atmospheric room temperature plasma (ARTP) mutation technology utilizes a principle of RF glow discharge, a high energy plasma is generated at a normal temperature and pressure. Active particles of the plasma act on the *Lactobacillus reuteri* to change a structure and a permeability of cell wall of the *Lactobacillus reuteri* and cause a gene damage, further a gene sequence and metabolic network of the *Lactobacillus reuteri* will be significantly changed, finally resulting in a mutation of the *Lactobacillus reuteri*. Compared with traditional mutation technologies, the ARTP technology adopted by the present application can effectively cause a diverse damage to DNA, a mutation rate is high and mutant strains with good genetic stability can be obtained easily.

The *Lactobacillus reuteri* with inactivated alcohol dehydrogenase is mutated, after mutation, inoculation culture is conducted again. Through testing, a concentrate of calcium propionate produced by the mutated *Lactobacillus reuteri* is higher, reaching nearly 27 g/L, and about three times as high as before the mutation.

Optionally, before the *Lactobacillus reuteri* with inactivated alcohol dehydrogenase is mutated, a preservation solution preserving with the *Lactobacillus reuteri* with inactivated alcohol dehydrogenase is diluted by using a normal saline.

Optionally, 25% calcium hydroxide is added into the fermentation culture medium to adjust a pH to 6-7.

Optionally, calcium carbonate is added into the fermentation culture medium.

In the above technical solutions, calcium carbonate is used as a buffer to maintain the pH in the fermentation culture medium.

Optionally, screening the mutated *Lactobacillus reuteri* with inactivated alcohol dehydrogenase in the fermentation culture medium, and repeatedly conducting enrichment culture and fermentation culture on screened strains.

In the above technical solutions, mutant strains with good genetic stability are obtained by screening, which are inoculated and cultured to obtain the mutated *Lactobacillus reuteri* producing calcium propionate.

Optionally, taking a fermentation liquid in the fermentation culture medium after fermentation culture and centrifuging the fermentation liquid to obtain a supernatant; and
  detecting the supernatant by a high performance liquid chromatography to obtain a content of calcium propionate.

In the above technical solutions, the concentration of calcium propionate of the *Lactobacillus reuteri* is tested by the HPLC.

In a second aspect, the present application provides an application of the method of producing calcium propionate by using *Lactobacillus reuteri* to calcium propionate, adopting the following technical solution:
  the method of producing calcium propionate by using *Lactobacillus reuteri* can produce calcium propionate.

In summary, the present application has the following beneficial technical effects:

1. Propionaldehyde is converted into 1-propanol under the action of the alcohol dehydrogenase, and in the present application, by inactivating the alcohol dehydrogenase of the *Lactobacillus reuteri*, this reaction is inhibited, and propionaldehyde is promoted to react towards a direction of producing propionyl coenzyme A. Meanwhile, it is also ensured that propionyl coenzyme A is promoted to react towards a direction of producing propionyl phosphonate. Finally, under a catalysis of the propionate kinase of the *Lactobacillus reuteri* with inactivated alcohol dehydrogenase, the propionyl phosphonate binds with calcium ion in the fermentation culture medium to produce calcium propionate.

Compared with a traditional method of producing calcium propionate, in the present application, a series of reactions are carried out by taking 1,2-propanediol as the substrate and the *Lactobacillus reuteri* as the catalytic agent, it is not only that a fermentation period is more than twice shorter than the traditional method of producing calcium propionate, but also a whole process does not require an anaerobic operation, which is a method of producing calcium propionate that can be widely used in general laboratories.

2. The genetically edited *Lactobacillus reuteri* with inactivated alcohol dehydrogenase is mutated by ARTP, after mutation, stable genetic mutant strains is obtained through multiple rounds of screening. Then, a fermentation optimization are conducted on the stains, so that the *Lactobacillus reuteri* producing high concentration of calcium propionate is obtained. Through a detection of the high performance liquid chromatography, it can be found that the concentration of calcium propionate produced by inactivated and mutated *Lactobacillus reuteri* is about 4 times that of calcium propionate produced by non-inactivated and non-mutated *Lactobacillus reuteri*.

BRIEF DESCRIPTION OF THE DRAWINGS

FIG. 1 shows an operation route of inactivating the alcohol dehydrogenase of the *Lactobacillus reuteri* by gene editing.

DETAILED DESCRIPTION

The present application is further described in detail below in combination with formulations of culture mediums and examples.

Formulation of Culture Mediums

Seed culture medium (MMRS): a solvent was water, and solutes and concentrations thereof were as follows respectively: 24 g/L of yeast powder, 24 g/L of glucose, 2.4 g/L of ammonium citrate, 6.2 g/L of sodium acetate, 1.8 g/L of dipotassium hydrogen phosphate, 0.16 g/L of manganese sulfate, 0.21 g/L of magnesium sulfate, and 0.8 g/L of polysorbate 80. A pH was 6.3 and a static culture was conducted at 37° C.

Fermentation culture medium: the solvent was water, and solutes and concentrations thereof were as follows respectively: 24 g/L of yeast powder, 7.6 g/L of 1,2-propanediol, 2.4 g/L of ammonium citrate, 6.2 g/L of sodium acetate, 1.8 g/L of dipotassium hydrogen phosphate, 0.16 g/L of manganese sulfate, 0.21 g/L of magnesium sulfate and 0.8 g/L of polysorbate 80. A culture temperature was 37° C., a rotation speed was 100 rpm and the pH was adjusted to 6.3 by using 25% calcium hydroxide emulsion.

Liquid culture medium: the solvent was water, and the solutes and concentrations thereof were as follows respectively: 24 g/L of yeast powder, 7.6 g/L of 1,2-propanediol, 2.4 g/L of ammonium citrate, 6.2 g/L of sodium acetate, 1.8 g/L of dipotassium hydrogen phosphate, 0.16 g/L of manganese sulfate, 0.21 g/L of magnesium sulfate and 0.8 g/L of polysorbate 80. The culture temperature was 37° C., the rotation speed was 100 rpm and the pH was adjusted to 6.3 by using 25% calcium hydroxide emulsion.

EXAMPLES

Example 1

By using a gene editing tool, a single base mutation was conducted on a alcohol dehydrogenase gene of the *Lactobacillus reuteri* to obtain genetically edited strains, which was preserved in a glycerol cryogenic vial.

Then, 1,2-propanediol was added into the glycerol cryogenic vial and mixed;

After mixed evenly, a genetically edited single colony was selected and streak inoculated on a MMRS solid plate, and cultured at 37° C. for 24 h.

Then, the single colony on the MMRS solid plate was selected and placed into the liquid culture medium, and statically cultured at 37° C. for 12 h.

The single colony in the liquid culture medium was selected according to 2% inoculation amount, and inoculated in the fermentation culture medium, and statically cultured at 37° C. for 24 h.

1 mL of a fermentation liquid was taken and centrifuged at 12000 rpm for 1 min, and an obtained supernatant was a sample to be tested.

The sample to be tested was tested by a high performance liquid chromatography (HPLC), parameters of the HPLC were set as follows AminexHPX-87H organic acid column, a mobile phase: 6 mmol/L $H_2SO_4$, a flow rate: 0.5 mL/min, a column temperature: 55° C. It was tested that a genetically edited *Lactobacillus reuteri* with inactivated alcohol dehydrogenase can produce calcium propionate with a concentrate of 9.75±0.15 g/L.

Example 2

By using the gene editing tool, the single base mutation was conducted on the alcohol dehydrogenase gene of the *Lactobacillus reuteri* to obtain the genetically edited strains, which was preserved in the glycerol cryogenic vial.

Then, 1,2-propanediol was added into the glycerol cryogenic vial and mixed;

After mixed evenly, the genetically edited single colony was selected and streak inoculated on the MMRS solid plate, and cultured at 37° C. for 24 h.

Then, the single colony on the MMRS solid plate was selected and placed into the liquid culture medium, and statically cultured at 37° C. for 8 h;

1 mL of a bacterial fluid was diluted to $10^7$ CFU/mL by using the normal saline, then the bacterial fluid was mutated according to an ARTP mutation technology. A mutated sample was diluted by using the normal saline again, and coated on the fermentation culture medium containing 5 g/L of calcium carbonate, then cultured at 37° C. for 24 h.

A preliminary screening was conducted according to a size of calcium dissolving zone in the fermentation culture medium, the strain with large calcium dissolving zone was streak inoculated on the MMRS solid plate, and cultured at 37° C. for 24 h;

A cultured single colony was selected and inoculated in the fermentation culture medium, and statically cultured at 37° C. for 8 h. A concentration of calcium propionate of mutant strain was tested by the HPLC, and parameters of the HPLC were set as follows AminexHPX-87H organic acid column, the mobile phase: 6 mmol/L $H_2SO_4$, the flow rate: 0.5 mL/min, the column temperature: 55° C.

Then strains with a highest concentration of calcium propionate were screened out, and 5 rounds of ARTP technology mutation and screening was repeatedly conducted on the strains, thereby one strain producing the highest concentration of calcium propionate was obtained.

The strain producing the highest concentration of calcium propionate was optimized by using a high cell-density culture process in a fermentation tank, and an optimized strain was streak inoculated on the MMRS solid plate, then cultured at 37° C. for 24 h;

the single colony in the MMRS solid plate was selected and inoculated in the liquid culture medium, and statically cultured at 37° C. for 12 h.

According to 2% inoculation amount, inoculation in the fermentation culture medium was conducted, and static culture was conducted at 37° C. for 24 h. 1 mL of the fermentation liquid was taken and centrifuged at 12000 rpm for 1 min, and the obtained supernatant was the sample to be tested.

The sample to be tested was tested by the HPLC, parameters of the HPLC were set as follows: AminexHPX-87H organic acid column, the mobile phase: 6 mmol/L $H_2SO_4$, the flow rate: 0.5 mL/min, the column temperature: 55° C. It was tested that the genetically edited *Lactobacillus reuteri* with inactivated alcohol dehydrogenase can produce calcium propionate with a concentrate of 27.6±0.35 g/L.

Comparative Example 1

A wild-type *Lactobacillus reuteri* was preserved in the glycerol cryogenic vial, and 1,2-propanediol was added into the glycerol cryogenic vial and mixed.

After mixed evenly, the strain liquid was dipped from the glycerol cryogenic vial and streaked on the MMRS solid plate, then cultured at 37° C. for 12 h. The single colony on the MMRS solid plate was selected and inoculated in the liquid medium, and statically cultured at 37° C. for 12 h, then were inoculated in the fermentation culture medium according to 2% inoculation amount, and statically culture at 37° C. for 24 h. 1 mL of a fermentation liquid was taken and centrifuged at 12000 rpm for 1 min, and the obtained supernatant was the sample to be tested.

The sample to be tested was tested by the HPLC, parameters of the HPLC were set as follows: AminexHPX-87H organic acid column, the mobile phase: 6 mmol/L $H_2SO_4$, the flow rate: 0.5 mL/min, the column temperature: 55° C. It was tested that the wild-type *Lactobacillus reuteri* can produce calcium propionate with a concentrate of 6.35±0.25 g/L.

The above are the preferred embodiments of the present application, which are not intended to limit the protection scope of the present application. Therefore, all equivalent changes made according to the structure, shape and principle of the present application should be covered within the protection scope of the present application.

What is claimed is:

1. A method of producing calcium propionate by using *Lactobacillus reuteri*, wherein the method comprises the following steps:
   conducting a single base mutation on an alcohol dehydrogenase gene of the *Lactobacillus reuteri* by using a gene editing tool to obtain *Lactobacillus reuteri* having an inactivated alcohol dehydrogenase;
   mutating the *Lactobacillus reuteri* having the inactivated alcohol dehydrogenase by an atmospheric room temperature plasma mutation technology to obtain a mutated *Lactobacillus reuteri* having an inactivated alcohol dehydrogenase;
   mixing the mutated *Lactobacillus reuteri* having the inactivated alcohol dehydrogenase with 1,2-propanediol, then growing and reproducing the mutated *Lactobacillus reuteri* having the inactivated alcohol dehydrogenase, and then conducting culture of the mutated *Lactobacillus reuteri* having the inactivated alcohol dehydrogenase; and
   after the culture, placing the mutated *Lactobacillus reuteri* having the inactivated alcohol dehydrogenase into a culture medium containing calcium ion for a fermentation culture, then obtaining the calcium propionate.

2. The method of producing calcium propionate by using *Lactobacillus reuteri* according to claim 1, wherein the mixing the mutated *Lactobacillus reuteri* having the inactivated alcohol dehydrogenase with the 1,2-propanediol, then growing and reproducing the mutated *Lactobacillus reuteri* having the inactivated alcohol dehydrogenase comprises:
   mixing the *Lactobacillus reuteri* having the inactivated alcohol dehydrogenase with the 1,2-propanediol, then growing and reproducing the mutated *Lactobacillus reuteri* having the inactivated alcohol dehydrogenase in a seed culture medium at a reproduction temperature of 37° C. for 24 h; wherein the seed culture medium comprises water as a solvent and 24 g/L of yeast powder, 24 g/L of glucose, 2.4 g/L of ammonium citrate, 6.2 g/L of sodium acetate, 1.8 g/L of dipotassium hydrogen phosphate, 0.16 g/L of manganese sulfate, 0.21 g/L of magnesium sulfate, and 0.8 g/L of polysorbate 80.

3. The method of producing calcium propionate by using *Lactobacillus reuteri* according to claim 1, wherein the conducting the culture comprises:

adopting a liquid culture medium for the culture at a culture temperature of 37° C.; wherein the liquid culture medium comprises water as a solvent and 24 g/L of yeast powder, 7.6 g/L of the 1,2-propanediol, 2.4 g/L of ammonium citrate, 6.2 g/L of sodium acetate, 1.8 g/L of dipotassium hydrogen phosphate, 0.16 g/L of manganese sulfate, 0.21 g/L of magnesium sulfate and 0.8 g/L of polysorbate 80.

4. The method of producing calcium propionate by using *Lactobacillus reuteri* according to claim 1, wherein the culture medium for the fermentation culture of the mutated *Lactobacillus reuteri* having the inactivated alcohol dehydrogenase is a fermentation culture medium, a temperature of the fermentation culture is 37° C., and a time of the fermentation culture is 24 h; wherein the fermentation culture medium comprises water as a solvent and 24 g/L of yeast powder, 7.6 g/L of the 1,2-propanediol, 2.4 g/L of ammonium citrate, 6.2 g/L of sodium acetate, 1.8 g/L of dipotassium hydrogen phosphate, 0.16 g/L of manganese sulfate, 0.21 g/L of magnesium sulfate and 0.8 g/L of polysorbate 80.

5. The method of producing calcium propionate by using *Lactobacillus reuteri* according to claim 4, wherein the method comprises the following step:
adding 25% calcium hydroxide into the fermentation culture medium to adjust a pH to 6-7.

* * * * *